(12) United States Patent
Sakamoto et al.

(10) Patent No.: US 6,599,397 B2
(45) Date of Patent: Jul. 29, 2003

(54) METHOD FOR PREVENTING POLYMERIZATION OF (METH)ACRYLIC ACID AND ESTERS THEREOF AND METHOD FOR THE PRODUCTION THEREOF

(75) Inventors: Kazuhiko Sakamoto, Himeji (JP); Tomohiro Nakae, Himeji (JP); Kazuo Okochi, Himeji (JP); Masahiro Uemura, Himeji (JP); Sei Nakahara, Himeji (JP)

(73) Assignee: Nippon Shokubai Co., Ltd. (JP)

( * ) Notice: Subject to any disclaimer, the term of this patent is extended or adjusted under 35 U.S.C. 154(b) by 40 days.

(21) Appl. No.: 09/875,541

(22) Filed: Jun. 6, 2001

(65) Prior Publication Data

US 2002/0002253 A1 Jan. 3, 2002

(30) Foreign Application Priority Data

Jun. 6, 2000 (JP) .................................... 2000-168726
Jun. 6, 2000 (JP) .................................... 2000-168727

(51) Int. Cl.[7] .............................. B01D 3/00; B01D 59/00
(52) U.S. Cl. ............................ 203/8; 560/205; 562/598
(58) Field of Search ....................... 203/8, 59, 29, 203/71; 562/600, 598; 560/205, 598; 252/404

(56) References Cited

U.S. PATENT DOCUMENTS 5,034,156 A * 7/1991 Varwig ........................ 203/8
5,322,960 A * 6/1994 Sakamoto et al. .......... 560/205
5,504,243 A   4/1996 Sakamoto et al.
5,824,195 A * 10/1998 Kimae et al. ................ 203/59
5,856,568 A   1/1999 Okamoto et al.
6,352,619 B1 * 3/2002 Fauconet et al. ............. 203/29

FOREIGN PATENT DOCUMENTS

| EP | 0 685 447 A2 | 6/1995 |
| EP | 0 765 856 A1 | 4/1997 |
| JP | A-8-48650 | 2/1996 |
| JP | A-9-95465 | 4/1997 |

* cited by examiner

*Primary Examiner*—Tatyana Zalukaeva
(74) *Attorney, Agent, or Firm*—Mathews, Collins, Shepherd & McKay, P.A.

(57) ABSTRACT

This method of preventing polymerization of methacrylic acid inn the process of its production is characterized by comprising using, in a refining column, a combination of N-nitrosophenylhydroxylamine or salt thereof with an N-oxyl compound, an N-hydroxy-,2,2,6,6-tetramethylpiperidine compound and a 2,2,6,6-tetramethylpiperidine compound. In this method, N-nitrosophenylhydroxylamine or a salt thereof rises inside a refining column under splitting part thereof to effectively inhibit polymerization of (meth)acrylic acid or the like. The above polymerization in both vapor and liquid phases can be inhibited more effectively by the combined use of the compounds mentioned above.

4 Claims, 1 Drawing Sheet

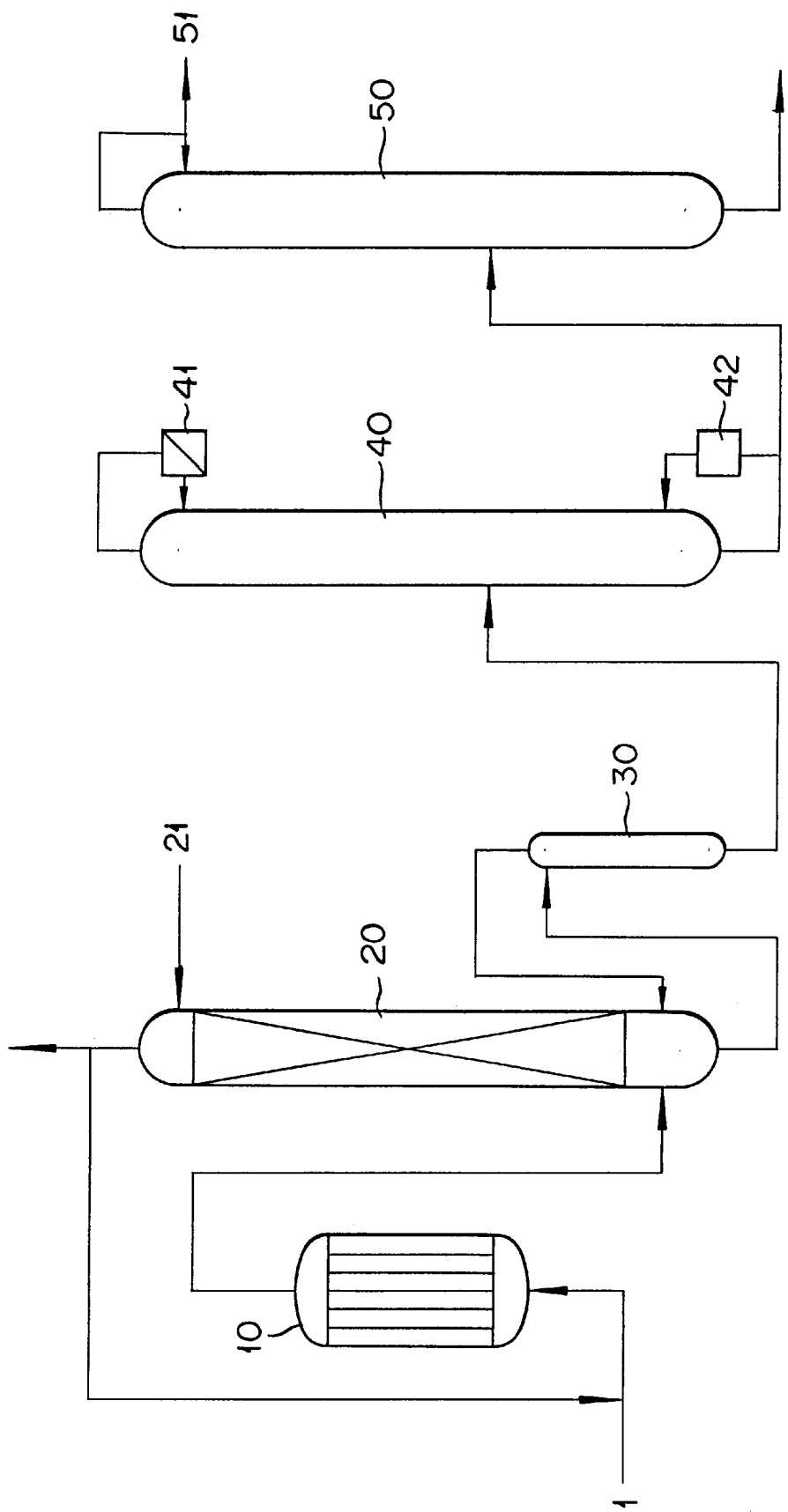
FIGURE

METHOD FOR PREVENTING POLYMERIZATION OF (METH)ACRYLIC ACID AND ESTERS THEREOF AND METHOD FOR THE PRODUCTION THEREOF

BACKGROUND OF THE INVENTION

1. Field of the Invention

This invention relates to a method for preventing (meth) acrylic acid and their esters from polymerizing and a method for the production thereof and more particularly to a method for preventing polymerization of (meth)acrylic acid and their esters, characterized by supplying an N-oxyl compound, an N-hydroxy-2,2,6,6-tetramethylpiperidine compound, a 2,2,6,6-tetramethylpiperidine compound, and an N-nitrosophenylhydroxylamine or a salt as a polymerization inhibitor to a distilling column and a method for the production of (meth)acrylic acid or their esters by including the method for the prevention of polymerization in the step of production. This invention also relates to a method for preventing polymerization of (meth)acrylic acid and their esters, characterized by using a nitroso compound as a polymerization inhibitor and performing the distillation in the column while supplying the polymerization inhibitor to the column from the bottom side of the column and a method for the production of (meth)acrylic acid and their esters, including the method for the prevention of the polymerization in the step of production.

2. Description of Related Arts

Such easily polymerizing compounds as acrylic acid and methacrylic acid are raw materials for commercial production and are chemical substances which are produced in a large amount at a plant of a large scale. In the case of (meth)acrylic acid, for example, the easily polymerizing compound is produced by the reaction of catalytic gas phase oxidation of propylene, isobutylene, t-butanol, methyl-t-butyl ether, or acrolein. The reaction gas obtained by the reaction of catalytic gas phase oxidation contains (meth) acrylic acid, the target product, as mixed with other by-products. For example, this reaction generates mainly non-condensable gases, namely unaltered propylene, isobutylene, and acrolein, low-boiling point organic compounds having lower boiling points than acrylic acid, namely steam and unaltered acrolein, formaldehyde produced by a secondary reaction, and impurities such as acetic acid, and high-boiling point compounds having higher boiling points than acrylic acid, namely maleic anhydride, furfural, benzaldehyde, benzoic acid, and acrylic acid dimer. For the purpose of purifying this reaction gas thereby producing the target product, therefore, it is generally for the reaction gas to wash with a counter flow water or a heavy solvent thereby effecting absorption of the gas and subsequently supplying the absorbed gas to a distilling column and purifying it therein.

(Meth)acrylic acid and esters thereof are compounds which possess a very easily polymerizing quality because of their structures. Moreover, since the process for the distillation of (meth)acrylic acid, for example, forms a system in which a gas phase part and a liquid phase part exist in a mixed state, it becomes necessary to prevent both the liquid phase part and the gas phase part in the distilling column effectively from polymerizing and enable the column to be continuously operated stably for a longtime. Generally, for the purpose of preventing the occurrence of such polymerization, various polymerization inhibitors are incorporated in the monomers either singly or in the form of a combination of several members to prevent the process of production from generating a polymer.

In the official gazette of U.S. Pat. No. 5,856,568, for example, discloses a method for preventing a vinyl compound from polymerizing by using an N-nitrosophenylhydroxylamine, i.e. one kinds of nitroso compound, or a salt, characterized by using the N-nitrosophenylhydroxylamine or the salt thereof in the presence of a copper salt compound. This method is claimed to prevent effectively the polymerization of acrylic acid or methacrylic acid and allow the process of production to be operated stably for a long time by introducing the both compounds mentioned above simultaneously or separately into the steps of distillation. In a working example adduced therein, the occurrence of a polymer was observed when a refluxing operation was performed after copper dibutyldithiocarbamate and N-nitrophenyl hydroxyl amine had been dissolved in acrylic acid.

The official gazette of JP-A-08-48,650 (relevant to U.S. Pat. No. 5,504,243) discloses a method for (meth)acrylic acid or a salt thereof from polymerizing by using together with an N-oxyl compound at least one polymerization inhibitor selected from among manganese salt compounds, copper salt compounds, 2,2,6,6-tetramethylpiperidine compounds, and nitroso compounds.

The method described in the official gazette of JP-A-09-95,465 (relevant to U.S. Pat. No. 5,856,568), however, uses a copper salt compound as an essential component and consequently suffers the used water containing the copper compound to be released into the environment. This method, herefore, is at a disadvantage in newly necessitating a means for the disposal of this polluted used water.

Further, for the purpose of effectively preventing (meth) acrylic acid from polymerizing, it suffices to increase the amount of the polymerization inhibitor. This measure, however, entails the disadvantage of necessitating a step for the removal of the polymerization inhibitor at the stage of an operation for polymerizing (meth)acrylic acid, for example.

The official gazette of U.S. Pat. No. 5,504,243 described working examples using a plurality of polymerization inhibitors in combination. The compound stated therein as actually used in combination with an N-nitrosophenylhydroxylamine or a salt thereof is limited to 4-hydroxy-2,2,6,6-tetramethylpiperidinooxyl.

Generally, for the purpose of separating such by-products as low-boiling point substances like acetic acid and some aldehyde and high-boiling point substances like furfural and maleic anhydride which are contained in the (meth)acrylic acid synthesized by the catalytic gas phase oxidation of propylene, for example, the (meth)acrylic acid-containing solution is subjected to distillation, dissipation, extraction, and crystallization. The process production, however, is required to be further simplified. Such in the true status of affairs, when the number of acetic acid separating columns or the number of steps of distillation is decreased by way of simplification, however, the decrease entails the necessity for rigidifying the conditions of distillation. Though the simplification of the process of production constitutes a demand from a social cause, it will be added an occurrence of generation of a polymer because it requires at each step of purification severer conditions of distillation than today. When the polymer is generated, the continuous operation of the purifying column is disabled and the work of removing the polymer from the purifying column is rendered more difficult.

In the light of this true state of affairs, the need for developing in connection with the production of such an easily polymerizing substance as (meth)acrylic acid a method for effectively preventing the occurrence of a polymer in both the gas phase and the liquid phase in a purifying column and consequently attaining continuous operation of the column required inherently and a method for producing the easily polymerizing substance has been earnestly felt.

SUMMARY OF THE INVENTION

The present inventors, as a result of pursuing an elaborate study on the function of a nitroso compound manifested in the prevention of polymerization, have found that an N-nitrosophenylhydroxylamine or a salt thereof is decomposed at least partly after it has been added to the step of distillation, the product of this decomposition contains what is possessed of the function of inhibiting polymerization and what is possessed of the function of promoting polymerization in a mixed state, the use of a known N-oxyl compound and other polymerization inhibitor in combination with the decompositions can promote the effect of preventing the polymerization of (meth)acrylic acid, etc., and the supply of the aforementioned compound via a specified point during the introduction thereof into a distilling column can promote the effect of preventing polymerization in the gas phase and repress the effect of the polymerization-promoting substance. This invention has been perfected as a result. Specifically, the object mentioned above is accomplished by the following items (1) to (3).

(1) A method for preventing the polymerization of (meth) acrylic acid and esters thereof, characterized by using an N-nitrosophenylhydroxylamine or a salt thereof in combination with an N-oxyl compound, an N-hydroxy-2,2,6,6-tetramethylpiperidine compound, and a 2,2,6,6-tetramethylpiperidine compound in a purifying column.

(2) The method described above, wherein the N-nitrosophenylhydroxylamine or the salt thereof, mentioned above is supplied to the purifying column from a level not higher than the position of 70% of the total number of theoretical plates, with the bottom side of the column as the base point.

(3) A method for the production of (meth)acrylic acid or an ester thereof, characterized by incorporating in the process of production the method for the prevention of the polymerization of (meth)acrylic acid and esters thereof as set forth in any of Items (1)–(2).

When the N-nitrosophenylhydroxylamine or the salt thereof is used in combination with an N-oxyl compound, an N-hydroxy-2,2,6,6-tetramethylpiperidine compound, and a 2,2,6,6-tetramethylpiperidine compound in accordance with this invention, the N-nitrosophenylhydroxylamine or the salt thereof is decomposed in a distilling column and the gas component consequently obtained effectively prevents the polymerization of the easily polymerizing substance existing in the gas phase of the interior of a purifying column and, at the same time, inhibits the polymerization of the easily polymerizing substance by allowing the presence of the N-oxyl compound in the liquid phase thereof. When the N-nitroso compounds mentioned above are supplied to the purifying column at a level not higher than the position of 70% of the total number of theoretical plates in this case, these compounds are decomposed in the distilling column and the gas component consequently obtained effectively prevents the polymerization of the easily polymerizing substance existing in the gas phase of the interior of a purifying column and, at the same time, inhibits the effect of the aforementioned polymerization promoting substance. Thus, the polymerization of the easily polymerizing substance in both the liquid phase and the gas phase can be synergistically inhibited.

The easily polymerizing compounds contemplated by this invention are (meth)acrylic acid and esters thereof which form both the gas and liquid phases in the interior of the purifying column.

When the (meth)acrylic acid and the esters thereof are produced by implementing the method of this invention for preventing the polymerization, the occurrence of a polymer the process of production is inhibited to permit continuous operation of the column and improve the yield of the product.

BRIEF DESCRIPTION OF THE DRAWINGS

FIGURE is a schematic flow diagram illustrating a process for the production of acrylic acid. In the diagram, 1 represents propylene, 10 a reaction vessel, 20 an acrylic acid absorption column, 21 an acrylic acid absorption liquid, 30 an acrolein separating column, 40 an azeotropic dehydrating column, 41 a tank, 42 a reboiler, 50 a high boiling separating column, and 51 acrylic acid.

DETAILED DESCRIPTION OF THE PREFERRED EMBODIMENTS

The first aspect of this invention consists in a method for preventing the polymerization of (meth)acrylic acid and esters thereof, characterized by using in a purifying column an N-nitrosophenylhydroxylamine or a salt thereof in combination with an N-oxyl compound, an N-hydroxy-2,2,6-6-tetramethylpiperidine compound, and a 2,2,6-6-tetramethylpiperidine compound.

As described above, the present inventors have discovered that the N-nitrosophenylhydroxylamine or the salt thereof is decomposed in the process for distilling (meth) acrylic acid and further that the gas component of the product of this decomposition manifest in the environment enclosed with the purifying column a function of preventing the polymerization of (meth)acrylic acid and the esters thereof. Particularly when the N-nitrosophenylhydroxylamine or the salt is supplied to the purifying column from the bottom side thereof, the gas component obtained in consequence of the decomposition in the environment enclosed with the purifying column easily mixes with the (meth)acrylic acid existing in the gaseous state while ascending the interior of the purifying column and, owing to the effect of the combined use thereof with the N-oxyl compound which is further contained, synergistically prevents the polymerization of an easily polymerizing substance.

In this invention, the term "purification" embraces distillation and dissipation. Here, the term "distillation" refers to a method for separating a volatile component contained in a solution by heating the solution till a boiling point and the term "dissipation" refers to a method for transferring a gas or a vapor dissolved in a solution to a gas phase by supplying a dissipating gas to the solution. Now, this invention will be described in detail below.

The method of this invention for preventing the polymerization of (meth)acrylic acid and esters thereof is aimed at preventing the polymerization which occurs in the purifying column during the purification of (meth)acrylic acid and the esters thereof. In spite of the designation, the purifying column is used in the process for the production of (meth)

acrylic acid and esters thereof. It, therefore, includes a wide variety of devices such as, distilling column, dissipating column, azeotropic separating column, dehydrating column, acetic acid separating column, light boiling substance separating column, and high boiling substance separating column which are used for the purpose of purifying or producing (meth)acrylic acid and esters thereof.

The conditions for purifying (meth)acrylic acid and esters thereof in the purifying column may be the same as the known conditions adopted for purifying or producing (meth) acrylic acid and esters thereof. This invention, however, does not need to be limited thereto.

The salt of the N-nitrosophenylhydroxylamine to be used in this invention is preferred to be an ammonium salt. The reason for this preference is that after the compound is decomposed under the conditions of the interior of the purifying column, the effect of the gas component manifested in inhibiting the polymerization of an easily polymerizing substance is particularly prominent.

This invention does not need to impose any particular limit on the site for the supply of the N-nitrosophenylhydroxylamine or a salt thereof. This compound may be supplied to the purifying column via the bottom part of the column, the middle stage of the column, or the top of the column. It is, however, preferred to be supplied to the purifying column from the bottom side thereof, particularly from "a level not higher than the position of 70% of the total number of theoretical plates, with the bottom side of the purifying column as the base point."

The position mentioned above means the interior of the purifying column at the position of not more than 70% of the total number of theoretical plates in the purifying column and all the pipes and accessorial devices attached thereto. The position of not higher than 70% of the total number of theoretical plates, therefore, ought to be interpreted as embracing the gas phase part and the bottom liquid in the purifying column and further embracing the reboiler attached to the purifying column and the pipes entering the reboiler and emanating from the reboiler. When a thin-film vaporizer is connected to the bottom part of the purifying column, therefore, the thin-film vaporizer itself and the pipes entering the thin-film vaporizer and emanating therefrom are embraced by the position for the supply of the nitroso compound contemplated by this invention. Properly, the position is in the range of 50–70%, more preferably in the range of 55–65%, of the total number of theoretical plates.

This invention has elected the supply of the N-nitrosophenylhydroxylamine or the salt thereof at a level of not higher than 70% of the total number of theoretical plates, with the bottom side of the purifying column as the base point on the basis of the discovery that the gaseous product of decomposition contains a portion manifesting the function of preventing the polymerization of an easily polymerizing substance in the gas phase and the nonvolatile product of decomposition contains a portion manifesting the function of promoting the polymerization.

Specifically, as described above, the present inventors have discovered that the compound mentioned above is decomposed during the process of distillation of (meth) acrylic acid, for example, and further that when the compound is introduced into the purifying column from the bottom side thereof, the gas component of the product of decomposition in the environment enclosed with the purifying column manifests the function of preventing the polymerization if (meth)acrylic acid and esters thereof in the gas phase. Particularly, when the compound is supplied to the purifying column from the bottom side thereof, the gas component obtained in consequence of the decomposition in the environment enclosed with the purifying column easily mixes with the (meth)acrylic acid existing in the gas state while ascending the interior of the purifying column and consequently prevents the polymerization of the relevant compounds effectively.

Such interior parts of a distilling column as trays, packing, liquid dispersing plate, flush feed liquid dispersing plate, primary liquid dispersing plate, collector, vapor dispersing plate, packing support, and packing bed retaining plate exists in the purifying column, are present in the purifying column. When the nonvolatile component which is the product of deposition of an N-nitrosophenylhydroxylamine or a salt thereof adheres to these interior parts, therefore, it possibly promotes the polymerization of (meth)acrylic acid on the surface of such interior parts. In this respect, the purifying column in the position of not higher than 70% of the total number of theoretical plates from the bottom side as the base point constitutes themselves the range for permitting the secondary function of effectively preventing the polymerization of the easily polymerizing gas in the gas phase and, at the same time, promoting the polymerization occurring on the surface of the interior parts.

The N-nitrosophenylhydroxylamine or a salt thereof is preferred, on account of the convenience of procedure, to be dissolved in a solvent and then delivered in the form of the resultant solution to the purifying column. To be specific, the N-nitrosophenylhydroxylamine or a salt thereof liquefied by being dissolved in a proper solvent, preferably the solvent which is incorporated in a reaction system, or the same solvent as the component incorporated in such liquid feed stock as water is supplied to the purifying column from the level in this position of not higher than 70% of the total number of theoretical plates, with the bottom side of the column as the base point. The solvent to be used for the purpose of dissolving the N-nitrosophenylhydroxylamine or the salt thereof may be suitably selected, depending on the conditions of the interior of the purifying column and the chemical and physical properties such as the solubility and decomposability of the N-nitrosophenylhydroxylamine or the salt thereof in the solvent. As concrete examples of the solvent, water, alcohol, hydrocarbon, ketone, ester, and acid may be cited. When the nitroso compound is the ammonium salt of N-nitrosophenylhydroxyloxylamine, water is most favorable in consideration of the stability in solvent and an acid is not favorable. Incidentally, when the step for supplying the raw material is included in the position, the raw material supplying solution incorporating therein the solution containing the N-nitrosophenylhydroxylamine or a salt thereof or the raw material supplying solution having the N-nitrosophenylhydroxylamine or a salt thereof dissolved therein may be introduced into the purifying column. The solution of the N-nitrosophenylhydroxylamine or the salt thereof may be advanced, dropped, or sprayed through the orifice penetrating the purifying column for the supply of the N-nitrosophenylhydroxylamine or the salt thereof.

The amount of the N-nitrosophenylhydroxylamine or the salt thereof to be supplied to the purifying column according to this invention does not need to be particularly discriminated. Since the compound is destined to be decomposed in the purifying column, the amount of the compound as reduced to the substance prior to the decomposition is such that the concentration of the N-nitrosophenylhydroxylamine or the salt thereof in the bottom liquid of the column is in the range of 0.0005–0.05 wt. %, preferably in the range of 0.001–0.01 wt. %. If this amount falls short of 0.0005 wt. %, the shortage will be at a disadvantage in providing no sufficient effect of preventing the polymerization. Incidentally, there is a time when the conditions of the purifying column possibly decomposes at least part of the N-nitrosophenylhydroxylamine or the salt thereof and the polymerization of (meth)acrylic acid is promoted, depending on the kind of the product of this decomposition. The polymerization can be inhibited by adjusting the concentration of the N-nitrosophenylhydroxylamine or the salt thereof in the bottom liquid of the column to below 0.05 wt. %.

This invention allows the N-nitrosophenylhydroxylamine or the salt thereof to be used in combination with an N-oxyl compound, an N-hydroxy-2,2,6,6-tetramethylpiperidine compound, and a 2,2,6,6-tetramethylpiperidine compound and further with such known polymerization inhibitors as phenol compound, phenothiazine compound, copper salt compound, and manganese salt compound. Since the product of decomposition of the N-nitrosophenylhydroxylamine or the salt thereof possibly promotes the polymerization as described above, the polymerization of (meth)acrylic acid particularly in the liquid phase can be prevented by such additional use of other polymerization inhibitor.

The N-oxyl compound to be used in this invention does not need to be particularly discriminated. Any of the N-oxyl compounds generally known as polymerization inhibitors for vinyl compounds can be used. In such known N-oxyl compounds, 2,2,6,6-tetramethylpiperidinooxyls represented by the following formula (1):

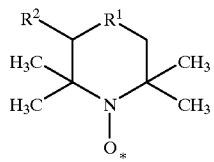

(wherein $R^1$ represents $CHOH$, $CHCH_2OH$, $CHCH_2CH_2OH$, $CHOCH_2OH$, $CHOCH_2CH_2OH$, $CHCOOH$, or $C=O$ and $R^2$ represents H or $CH_2OH$) are favorably used. Though any N-oxyl compound at all can be used without any particular restriction, it is proper to use one or more compounds selected from the group consisting of 2,2,6,6-tetramethylpiperadinooxyl, 4-hydroxy-2,2,6,6-tetramethylpiperidinooxyl, and 4,4',4"-tris-(2,2,6,6-tetramethylpiperidinooxyl) phosphite which can afford a satisfactory effect in preventing polymerization. Particularly, when 2,2,6,6-tetramethylpiperadinooxyl or 4-hydroxy-2,2,6,6-tetramethylpiperidinooxyl is used as the N-oxyl compound, the possibility of the stabilizer corroding the metallic devices is eliminated and the disposal of the waste liquid is facilitated because the stabilizer system is established without requiring the component to contain any metal.

As typical examples of the N-hydroxy-2,2,6-6-tetramethyl piperidine compound to be used in this invention, 1,4-dihydroxy-2,2,6,6-tetramethylpiperidine, 1-hydroxy-2,2,6,6-tetramethylpiperidine, etc. may be cited. These N-hydroxy-2,2,6,6-tetramethylpiperidine compounds may be used either singly or in the form of a mixture of two or more members.

As concrete examples of the 2,2,6,6-tetramethylpiperidine compound to be used in this invention, 2,2,6,6-tetramethylpiperidine, 4-hydroxy-2,2,6,6-tetramethylpiperidine, etc. maybe cited. At least one of these compounds may be used. Incidentally, N-hydroxy-2,2,6-6-tetramethylpiperidine compounds and 2,2,6,6-tetramethylpiperidine compounds are possibly contained as impurities in the commercially available products of N-oxyl compounds. In this case, the use of a commercially available N-oxyl compound means use of this compound in combination with N-hydroxy-2,2,6,6-tetramethylpiperidine compound and 2,2,6,6-tetramethylpiperidine compound of this invention.

In this invention, it is particularly favorable to use N-nitrosophenylhydroxylamine or a salt thereof in combination with an N-oxyl compound and further with an N-hydroxy-2,2,6,6-tetramethylpiperidine compound and a 2,2,6,6-tetramethylpiperidine compound. The reason for the commendableness is that these compounds for additional use particularly excel in effecting the inhibition of the polymerization of (meth)acrylic acid and esters therein in the liquid phase and, as a whole, accomplish synergistic inhibition of the polymerization in the gas and liquid phases in the purifying column.

In the case of such combined use of the N-nitrosophenylhydroxylamine or a salt with an N-oxyl compound and so on, the site for the supply of the N-oxyl compound, an N-hydroxy-2,2,6,6-tetramethylpiperidine compound, and a 2,2,6,6-tetramethylpiperidine compound does not need to be particularly limited. They may be supplied to the bottom of the column via a reboiler, they may be supplied together with the feed material into the purifying column through the feed orifice for the feed material, or they may be supplied to the top of the column or into the condenser attached to the column and then introduced into the distilling column through the medium of a reflux liquid. More preferably, they are introduced through the part of the purifying column higher than the step for the supply of the feed material. The expression "the part higher than the step for supply" as used herein embraces the supply from the condenser attached to the purifying column or the storing column which is used in separating the distillate into an oil phase and a water phase. Particularly favorably, this supply is made from the top part of the column, the interior of the condenser, the storing column, or the reflux liquid in the condenser or the storing column. For the purpose of enabling the polymerization inhibitor supplied to the purifying column to manifest the function of preventing polymerization most effectively, it is necessary that (1) the polymerization inhibitor exhibit thorough solubility in the liquid phase, (2) with a view to enabling the polymerization inhibitor supplied to the purifying column in which the composition of the internal liquid thereof varies with the relative position in the interior of the column to retain the composition mentioned above, the polymerization inhibitor be supplied in the liquid composition most similar to the internal composition of the column, and (3) the position of the polymerization inhibitor be such as to enable itself to be most effectively mixed with the liquid phase, i.e. the target for polymerization inhibitor. Here, since the N-oxyl compound is a powder, the supply thereof to the interior of the purifying column is preferred to be effected by a procedure which comprises dissolving this compound in a solvent and then introducing the resultant solution into the column. It is commendable, for example, to prepare the solution containing the compound by using part of the solvent which is supplied to the interior of the purifying column. When the position for introducing the polymerization inhibitor-containing solution is selected in the range in which the concentration of the solvent in this solution is similar to the concentration of the solvent in the interior liquid of the purifying column, the composition of the interior liquid of the column does not need to be varied. The condition for the selection of this position cannot be uniquely decided in accordance with the condition of distillation, the condition of dissipation, etc. in the interior of the purifying column. In the case of the N-oxyl compound, the position selected in the part higher than the step for the supply of the feed stock excels in producing the effect of preventing polymerization.

Besides being supplied as dissolved in a solvent, the N-oxyl compound may be supplied in a solidified state or in a gasified state to the purifying column. As regards the method for causing this compound to function in a dissolved state, for example, the polymerization initiator liquefied by being dissolved in a proper solvent may be supplied to the condenser or the storing tank attached to the purifying column besides being supplied to the purifying column through the top of the column. Depending on the type of the condenser, the solution containing the polymerization inhibitor may be placed in the interior of the condenser and the gaseous distillate may be blown therein or the liquefied distillate may be cast therein to be dissolved therein. This procedure can effectively prevent the polymerization in the condenser. As concerns the method for causing the compound to function in the gasified state, the polymerization inhibitor may be gasified or sublimed and the resultant gas may be supplied to the path interconnecting the purifying column and the condenser and mixed therein with the inner liquid.

The solvent which is capable of dissolving the polymerization inhibitor mentioned above is preferred to be the solvent which is supplied to the interior of the purifying column as described above or the reflux liquid from the condenser attached to the column. As concrete examples of the solvent to be supplied to the purifying column, benzene, toluene, xylene, cyclohexane, acetone, methylethyl ketone, methylisobutyl ketone, n-hexane, heptane, and mixtures thereof may be cited. Since these solvents are variable with the condition prevailing in the purifying column, the most preferred solvent for dissolving the polymerization inhibitor is selected based on the solvent actually used. When the solvent to be used in the purifying column is adopted, this solvent is at an advantage in excelling in mixing with the easily polymerizing substance and the polymerization inhibitor and enabling the composition of the interior liquid of the column to be retained intact. If a different solvent is used, it will be at a disadvantage in necessitating the solvent to be recovered separately. If the separation is attained by the reflux to the reaction system, it will be at a disadvantage in complicating the control and management of the reaction system.

As concrete examples of the phenol compound which can be additionally used in this invention, hydroquinone and p-methoxyphenol may be cited. p-Methoxyphenol is at an advantage in excelling hydroquinone in the effect of preventing polymerization particularly when it is used in combination with an N-oxyl compound and a phenothiazine compound. These phenol compounds may be used in the form of a combination of two or more members.

As concrete examples of the phenothiazine compound, phenothiazine, bis-(α-methylbenzyl)phenothiazine, 3,7-dioctylphenothiazine, and bis-(α-dimethylbenzyl)phenothiazine may be cited. Among other phenothiazine compounds enumerated above, phenothiazine is used particularly favorably. These phenothiazine compounds may be used in the form of a combination of two or more members.

Though the metal compound salt requires to ensure the preservation of the environment because it has a corroding function and the possibility of separating itself when it is released into the environment after use, it can be additionally used in this invention.

The copper salt compounds do not need to be particularly discriminated and they may be either inorganic salts or organic salts. Various copper salt compounds are usable. As concrete examples of the copper salt compound, copper dialkyldithiocarbamates, copper acetate, copper naphthenate, copper acrylate, copper sulfate, copper nitrate, and copper chloride may be cited. These copper salt compounds may be used in a monovalent form or a divalent form. In the copper salt compounds enumerated above, copper dialkyldithiocarbamate proves favorable from the viewpoint of the effect.

As concrete examples of the copper dialkyldithiocarbamate, copper dimethyldithiocarbamate, copper diethyldithiocarbamate, copper dipropyldithiocarbamate, copper dibutyldithiocarbamate, copper dipentyldithiocarbamate, copper dihexyldithiocarbamate, copper diphenyldithiocarbamate, copper methylethyldithiocarbamate, copper methylpropyldithiocarbamate, copper methylbutyldithiocarbamate, copper methylpentyldithiocarbamate, copper methylhexyldithiocarbamate, copper methylphenyldithiocarbamate, copper methylpropyldithiocarbamate, copper ethylbutyldithiocarbamate, copper ethylpentyldithiocarbamate, copper ethylhexyldithiocarbamate, copper ethylphenyldithiocarbamate, copper propylbutyldithiocarbamate, copper propylpentyldithiocarbamate, copper propylhexyldithiocarbamate, copper propylphenyldithiocarbamate, copper butylpentyldithiocarbamate, copper butylhexyldithiocarbamate, copper butylphenyldithiocarbamate, copper pentylhexyldithiocarbamate, copper pentylphenyldithiocarbamate, and copper hexylphenyldithiocarbamate may be cited. Such dialkyldithiocarbamates may be monovalent copper salts or divalent copper salts. Among other copper dialkyldithiocarbamates enumerated above, copper dimethyldithiocarbamate, copper diethyldithiocarbamate, and copper dibutyldithiocarbamate prove favorable and copper dibutyldithiocarbamate proves particularly advantageous from the viewpoint of the effect and the availability.

As concrete examples of the manganese salt compound, manganese dialkyldithiocarbamates (the alkyl group may be any of methyl, ethyl, propyl, and butyl and, in the occurrence of a plurality of alkyl groups, may be the same or different), manganese diphenyldithiocarbamate, manganese formate, manganese acetate, manganese octanoate, manganese naphthenate, and manganates of ethylenediamine tetraacetic acid may be cited. These manganese salt compounds may be used either singly or in the form of a combination of two or more members. The manganese salt compound, when used solely, has a (comparatively low function of preventing polymerization. It has been demonstrated, however, that when it is used in combination with an N-oxyl compound and further with other polymerization inhibitor, manifests a prominent effect of preventing polymerization. Though the copper compound has a corroding function, it is at an advantage in repressing the corroding function when it has a manganese salt compound added thereto.

In this invention, the supply of the phenol compound, the copper salt compound, and the manganese salt compound to the purifying column is favorably attained by introducing them into the purifying column from the part higher than the step for supply of the feed stock similarly to the supply of the N-oxyl compound. From the viewpoint of the solubility of this compound in the solvent, these compounds easily mix with the easily polymerizing compound and enable the operation of purification to be continued without causing any change in the composition of the internal liquid of the purifying column similarly to the addition of the N-oxyl compound. The polymerization inhibitors to be used in a combined state may be introduced wholly through one and the same position of supply or individually through different positions of supply. Further, the time for the supply does not need to be particularly restricted. For example, the N-oxyl compound may be supplied through the top of the column and the manganese salt compound may be supplied through the middle state of the purifying column. When the manganese salt compound sparingly soluble in an organic solvent is used and when the concentration of the organic solvent is high on the top side of the purifying column, the change of the composition of the internal liquid of the column can be decreased by effecting the supply in the neighborhood of the intermediate stage of the column. When the manganese salt compound is easily soluble in an organic solvent and is sparingly soluble in water, therefore, the supply of the compound through the top of the purifying column can efficiently bring the expected function of preventing polymerization. In any event, the optimum position of supply is selected in consideration of the solubility of the added polymerization inhibitor in the solvent and the environment enclosed with the purifying column, particularly the composition of the interior liquid of the column.

Incidentally, when the polymerization inhibitor to be used in this invention itself is a liquid and even when it has no sufficient mutual solubility with the internal composition of the column, the supply through the top of the column is allowable so long as the transfer thereof via the structural components in the column encounters no hindrance from the viewpoint of viscosity or reactivity.

The method of this invention for the prevention of polymerization can be favorably used for (meth)acrylic acid and esters thereof which particularly tend to polymerize among other vinyl compounds. As concrete examples of the acrylic esters to which the method is applied, methyl acrylate, ethyl acrylate, butyl acrylate, 2-ethylhexyl acrylate, 2-hydroxyethyl acrylate, and 2-hydroxypropyl acrylate may be cited. As concrete examples of the methacrylic esters to which the method is applied, methyl methacrylate, butyl methacrylate, 2-hydroxyethyl methacrylate, and 2-hydroxypropyl methacrylate may be cited.

The method for preventing polymerization will be explained below by adducing the case of producing (meth) acrylic acid by the reaction of catalytic gas phase oxidation, for example. This method is implemented by causing the polymerization inhibitor mentioned above to coexist with the (meth)acrylic acid at the varying steps of distillation as in the rectifying column for (meth)acrylic acid, the separating column for the (meth)acrylic acid and the solvent, and the separating column for the (meth)acrylic acid and such a light boiling point component as acetic acid and at various steps embracing the operation of distillation as in the stripper for such a light boiling point component as acrolein or methacrolein.

Particularly, in the process for distillation which obtains acrylic acid substantially free from acetic acid, water, and an azeotropic solvent from the bottom of an azeotropic separating column by the so-called sole operation of distillation i.e. by introducing an aqueous acrylic acid solution containing such impurities as acetic acid into the azeotropic separating column and expelling the acetic acid in conjunction with the azeotropic solvent and water through the top of the column, the present invention especially fits the purpose of effectively preventing the polymerization in an azeotropic dehydrating column, enabling the prevention of polymerization to last a long time, and ensuring stable production of the acrylic acid. By this invention, it is made possible to prevent effectively the occurrence of a polymer in the various steps of purification which are liable to rigidify the conditions of separation and induce polymerization in consequence of the simplification of the princess for the production of (meth)acrylic acid or an ester thereof.

Specifically, the conditions of distillation which set the reflux ratio in the azeotropic dehydrating column in the range of 1.1–1.6, more preferably in the range of 1.2–1.5, and particularly preferably in the range of 1.3–1.5 may be adopted, for example, when acrylic acid substantially free from acetic acid, water, and an azeotropic solvent by the so-called sole operation of distillation, i.e. by bringing the acrylic acid-containing gas obtained by catalytic gas phase oxidation of propylene and/or acrolein into contact with water thereby forming an aqueous acrylic acid solution containing such impurities as acetic acid and introducing this acrylic acid-containing aqueous solution into the azeotropic dehydrating column. If the reflux ratio falls short of 1.1, the shortage will be at a disadvantage in increasing the expulsion of acrylic acid by evaporation through the top of the column. If the reflux ratio exceeds 1.6, the excess will be at a disadvantage in adding to the concentration of the azeotropic solvent in the bottom of the column. In this case, the column top temperature is preferred to be controlled in the range of 45–55° C. If this temperature falls short of 45° C., the shortage will be at a disadvantage in suffering the distillation gas emanating from the top of the column to cool and consequently necessitating addition of a new cooling device. Converse, if the temperature exceeds 55° C., the excess will be at a disadvantage in increasing the amount of acrylic acid expelled by evaporation through the top of the column. Then, the column bottom temperature is preferred to be controlled in the range of 100–110° C. If the temperature exceeds 110° C., the excess will be at a disadvantage in increasing the dimer of acrylic acid in the bottom liquid of the column and lowering the yield of the acrylic acid.

Then, the conditions of distillation which set the acetic acid concentration in the bottom liquid of the column below 0.1 wt. %, more preferably below 0.05 wt. %, and particularly preferably below 0.03 wt. %.

This invention can be adapted to all the harsh conditions of distillation as in the step for distillation using high operating temperatures even in the devices other than the azeotropic dehydrating column and the step of distillation handling a plurality of polymerizing substances. As the step for distillation using a high operating temperature, the step of distillation which comprises bringing the acrylic acid-containing gas obtained by the reaction of catalytic gas phase oxidation of propylene into contact with a high boiling point organic solvent, collecting the resultant acrylic acid-containing solution, and then separating the high boiling point organic solvent from the acrylic acid-containing solution may be cited, for example. As the step for purification handling a plurality of polymerizing substances, the distillation of a three-component system containing acrylic acid, an acrylic ester, and water may be cited, for example.

The total amount of the polymerization inhibitors does not need to be particularly limited but may be properly adjusted to suit the prevalent operating condition. The total amount of the polymerization inhibitors to be used is preferred to be in the range of 3–1500 ppm (on weight basis) based on the amount of (meth)acrylic acid and the ester thereof to be expelled by evaporation. As respect the preferred amount of use of a varying polymerization inhibitor, the amount of an N-oxyl compound is in the range of 1–500 ppm based on the amount of the vapor of the monomer produced by evaporation, that of a manganese salt compound or a copper salt compound is in the range of 1–200 ppm based on the amount of the vapor of the monomer produced by evaporation, and that of a 2,2,6,6-tetramethylpiperidine compound or an N-nitrosophenylhydroxylamine or a salt thereof in the range of 1–500 ppm based on the amount of the vapor of the monomer formed by evaporation.

The expression "amount of vapor formed by evaporation" as used herein means the total amount of the vapor of the monomer form in the reboiler, depending on the amount of heat applied to the reboiler of the distilling column. The total amount of the vapor of the monomer can be easily found by calculation. This total amount constitutes itself a numeral which serves an important factor in the decision of the standard for the introduction of the polymerization inhibitor.

In this invention, molecular oxygen may be supplied as the polymerization inhibitor to the interior of the purifying column. The supply of this molecular oxygen may be effected as by air bubbling so as to mix this oxygen directly with (meth)acrylic acid and ester thereof. The oxygen may otherwise be mixed indirectly with (meth)acrylic acid and ester thereof in the form dissolved in other solvent. Incidentally, when the molecular oxygen is delivered in a gaseous state via the bottom of the purifying column or the stripper and/or the reboiler, and air bubbling can be easily incorporated in the process for production. Advisably, the molecular oxygen is introduced in an amount in the approximate range of 0.1–1.0 vol. %, based on the amount of the vapor of the (meth)acrylic acid or an ester thereof produced by evaporation.

The second aspect of this invention consists in a method for the production of (meth)acrylic acid or esters thereof, characterized by incorporating in the process of production the aforementioned method for preventing polymerization of (meth)acrylic acid and esters thereof.

The (meth)acrylic acid and esters thereof are continuously produced generally past various steps of purification called a absorption column, a dehydrating column, a light boiling separating column a high boiling separating column, an acetic acid separating column, an ester reaction vessel, and a dehydrating column which follow the reaction vessel for catalytic gas phase oxidation.

The conditions for the operation of the purifying columns to be used at these steps are variable with the conditions for the operation of the purifying columns preceding or following them and cannot be uniquely defined. This invention, however, finds it advisable to perform the method of this invention for the prevention of polymerization particularly in the azeotropic dehydrating column for removing water from the (meth)acrylic acid-containing solution formed as described above by collecting (meth)acrylic acid with a water type solvent or, in addition thereto, in the low boiling separating column for separating such low boiling substances as aldehyde and acetic acid. Generally, these are steps which are most liable to induce polymerization of (meth)acrylic acid and, therefore, becomes a rate determination step for the production of the compound. Thus, this invention proves particularly effective for these steps.

The method for the production of (meth)acrylic acid which has the method of this invention for the prevention of polymerization incorporated at least in part not only prevents the occurrence of a polymer in the purifying column and permits the operation of the column to be continued for a long time but also improves the yield of the product. In this respect, the method of this invention for the production of (meth)acrylic acid and esters thereof prefers the method of this invention for the prevention of polymerization to be applied to each of the purifying columns used in the process of production.

EXAMPLES

Now, this invention will be described more specifically with reference to working examples.

Example 1

Acrylic acid was produced in accordance with the production process for acrylic acid which is illustrated in Figure.

First, propylene and a molecular oxygen-containing gas were supplied to a catalytic gas phase reaction vessel 10 provided with an intermediate tube sheet partitioning the reaction vessel into an upper and a lower chamber to obtain an acrylic acid-containing gas in consequence of catalytic gas phase oxidation, introducing this acrylic acid-containing gas into an acrylic acid absorption column 20, and brought therein into contact with water to absorb the acrylic acid in an aqueous solution. This acrylic acid-containing solution contained acrolein as an impurity. The acrylic acid-containing solution mentioned above was introduced into an acrolein dissipating column 30 to effect dissipation of acrolein and obtain an aqueous acrylic acid solution containing 30 wt. % of water and 3.0 wt. % of acetic acid.

This aqueous acrylic acid solution was introduced into an azeotropic separating column 40 measuring 105 mm in inside diameter and provided with 50 stepped stainless steel-made sieve trays spaced at intervals of 147 mm and provided in the top part of the column with distillation pipes and reflux supply pipes, in the central part of steps (20 steps) with a material supplying pipe and a polymerization inhibiting agent inlet pipe, and in the bottom part of the column with a column bottom extraction pipe and a polymerization inhibitor inlet pipe to distill the aqueous acrylic acid solution with toluene as an azeotropic solvent.

The amount of the polymerization inhibitor to be used was 100 ppm in the case of 4-hydroxy-2,2,6,6-tetramethylpiperidinooxyl, 20 ppm in the case of 1,4-dihydroxy-2,2,6,6-tetramethylpiperizine, 20 ppm in the case of 4-hydroxy-2,2,6,6-tetramethylpiperidine, and 20 ppm in the case of the ammonium salt of N-nitrosophenylhydroxylamine respectively, relative to the amount of the vapor of acrylic acid formed by evaporation. The ammonium salt of N-nitrosophenylhydroxylamine was supplied into the interior of the column in the form dissolved in water via the bottom of the column and other polymerization inhibitor in the form dissolved in a reflux liquid via the top of the column. Further,the molecular oxygen was supplied to the bottom part of the column in an amount of 0.3 vol. % based on the amount of the vapor of the acrylic acid formed by evaporation. The expression "amount of the vapor of acrylic acid formed by evaporation" as used herein means the total amount of the vapor of the monomer expelled by evaporation through the bottom of the column in proportion to the amount of heat applied to a reboiler 42 of an azeotropic dehydrating column 40.

As respects the operating conditions during the stationary operation, the temperature of the top of the azotropic separating column 40 was 50° C., the temperature of the bottom of the column was 105° C., the pressure in the top of the column was 170 hPa, the reflux ratio (the total number of mols of the reflux liquid per unit time/the total number of mols of the distillate per unit time) was 1.43, and the amount of the aqueous acrylic acid solution supplied was 8.5 liters/hr. The water phase expelled by distillation via the top of the azeotropic dehydrating column 40 contained 7.5 wt. % of acetic acid and 1.8 wt. % of acrylic acid and the liquid extracted via the bottom of the column contained 97.5 wt. % of acrylic acid, 0.03 wt. % of acetic acid, 0.02 wt. % of water, and 2.45 wt. % of other components. The content of toluene was less than the limit of detection (1 ppm).

When the azeotropic dehydrating column 40 was continuously operated under the conditions mentioned above for 60 days, a constantly stable state was obtained. When the operation was stopped and the interior of the distilling column was inspected, absolutely no sign of the occurrence of a polymer was recognized.

Example 2

The kinds and the amounts of polymerization inhibitor were 100 ppm of 4-hydroxy-2,2,6,6-tetramethylpiperidinooxyl, 20 ppm of 1,4-dihydroxy-2,2,6,6-tetramethylpiperidine, 20 ppm of 4-hydroxy-2,2,6,6-tetramethylpiperidine, and 10 ppm of the ammonium salt of N-nitrosophenylhydroxylamine, respectively relative to the amount of the vapor of acrylic acid formed by evaporation. Acrylic acid was produced by following the procedure of Example 1 while having the ammonium salt of N-nitrosophenylhydroxylamine dissolved in water and then supplied to the azeotropic dehydrating column 40 via the bottom thereof and the other polymerization inhibitors invariably dissolved in the reflux liquid and then supplied to the column via the top thereof. Further, molecular oxygen was supplied to the bottom part of the column in an amount of 0.3 vol. % relative to the amount of the vapor of acrylic acid formed by evaporation. Incidentally, the expression "amount of the vapor of acrylic acid formed by evaporation" as used herein means the total amount of the vapor of the monomer expelled by evaporation through the bottom of the column proportionately to the amount of heat applied from the reboiler 42 of the azeotropic dehydrating column 40.

As respects the operating conditions during the stationary operation, the temperature of the top of the azeotropic separating column 40 was 50° C., the temperature of the bottom of the column was 105° C., the pressure in the top of the column was 170 hPa, the reflux ratio (the total number of mols of the reflux liquid per unit time/the total number of mols of the distillate per unit time) was 1.20, and the amount of the aqueous acrylic acid solution supplied was 9.0 liters/hr. The liquid extracted from the bottom of the column contained 97 wt. % of acrylic acid, 0.02 wt. % of water, and 2.98 wt. % of other components.

When the azeotropic dehydrating column 40 was continuously operated under the conditions mentioned above for 30 days, a constantly stable state was obtained. When the operation was stopped and the interior of the distilling column was inspected, a small amount of a polymer was recognized in the column and the column was found to be capable of further continuing operation.

Example 3

An aqueous acrylic acid solution was subjected to an operation of azeotropic distillation by following the procedure of Example 2 while changing the position for the introduction of the aqueous solution of the ammonium salt of N-nitrosophenylhydroxylamine from the bottom of the column to the position of 25% of the total number of theoretical plates with the bottom side of the column as the basic point.

When the azeotropic separating column 40 was continuously operated under the conditions for 30 days, the same state of separation as formed in Example 2 was obtained. When the operation was stopped and the interior of the distilling column was inspected, virtually no sign of the occurrence of a polymer was recognized.

Example 4

An aqueous acrylic acid solution was subjected to an operation of azeotropic distillation by following the procedure of Example 2 while changing the position for the introduction of the aqueous solution of the ammonium salt of N-nitrosophenylhydroxylamine from the bottom of the column to the position of 60% of the total number of theoretical plates with the bottom side of the column as the basic point.

When the azeotropic separating column 40 was continuously operated under the conditions for 30 days, the same state of separation as formed in Example 2 was obtained. When the operation was stopped and the interior of the distilling column was inspected, absolutely no sign of the occurrence of a polymer was recognized.

Example 5

An aqueous acrylic acid solution was subjected to an operation of azeotropic distillation by following the procedure of Example 1 while using 4-hydroxy-2,2,6,6-tetramethylpiperidinooxyl in an amount of 50 ppm, 1,4-dihydroxy-2,2,6,6-tetramethylpiperidine in an amount of 10 ppm, 4-hydroxy-2,2,6,6-tetramethylpiperidine in an amount of 10 ppm, and the ammonium salt of N-nitrosophenylhydroxylamine in an amount of 5 ppm respectively instead.

When the azeotropic separating column 40 was continuously operated under the conditions for 10 days, the same state of separation as formed in Example 1 was obtained. When the operation was stopped and the interior of the distilling column was inspected, absolutely no sign of the occurrence of a polymer was recognized.

Example 6

An aqueous acrylic acid solution was subjected to an operation of azeotropic distillation by following the procedure of Example 5 while changing the position for the introduction of the aqueous solution of the ammonium salt of N-nitrosophenylhydroxylamine from the bottom of the column to the position of 25% of the total number of theoretical plates with the bottom side of the column as the basic point.

When the azeotropic separating column 40 was continuously operated under the conditions for 10 days, the same state of separation as formed in Example 1 was obtained. When the operation was stopped and the interior of the distilling column was inspected, substantially no sign of the occurrence of a polymer was recognized.

Example 7

An aqueous acrylic acid solution was subjected to an operation of azeotropic distillation by following the procedure of Example 5 while changing the position for the introduction of the aqueous solution of the ammonium salt of N-nitrosophenylhydroxylamine from the bottom of the column to the position of 60% of the total number of theoretical plates with the bottom side of the column as the basic point.

When the azeotropic separating column 40 was continuously operated under the conditions for 10 days, the same state of separation as formed in Example 1 was obtained. When the operation was stopped and the interior of the distilling column was inspected, absolutely no sign of the occurrence of a polymer was recognized.

Example 8

An aqueous acrylic acid solution was subjected to an operation of azeotropic distillation by following the procedure of Example 5 while changing the position for the introduction of the aqueous solution of the ammonium salt of N-nitrosophenylhydroxylamine from the bottom of the column to the position of 80% of the total number of theoretical plates with the bottom side of the column as the basic point.

When the azeotropic separating column 40 was continuously operated under the conditions for 10 days, the same state of separation as formed in Example 1 was obtained. When the operation was stopped and the interior of the distilling column was inspected, the occurrence of 11 g of a polymer was recognized in the column. The column was capable of further continuing the operation.

Example 9

An aqueous acrylic acid solution was subjected to an operation of azeotropic distillation by following the procedure of Example 5 while changing the position for the introduction of the aqueous solution of the ammonium salt of N-nitrosophenylhydroxylamine from the bottom of the column to the top of the column.

When the azeotropic separating column 40 was continuously operated under the conditions for 10 days, the same state of separation as formed in Example 1 was obtained. When the operation was stopped and the interior of the distilling column was inspected, the occurrence of 25 g of a polymer was recognized in the column. The column was capable of further continuing the operation.

Comparative Example 1

An aqueous acrylic acid solution was subjected to an operation of azeotropic distillation by following the procedure of Example 1 while changing the amount of 4-hydoxy-2,2,6,6-tetramethylpiperidinooxyl to be used to 20 ppm and omitting the use of 1,4-dihydroxy-2,2,6,6-tetramethylpiperidine.

When the azeotropic separating column 40 was continuously operated under the conditions, the same state of separation as formed in Example 1 was obtained during the initial stage of operation. On the 17th day of starting the operation, the pressure drop of the column inside was recognized. On the 17th day of starting the operation, the pressure loss was recognized in the column. On the 20th day of the operation, the operation could be continued only with difficulty. When the operation was stopped and the distilling column was disassembled and inspected, the occurrence of a large amount of a polymer was recognized in the stripping section of the interior of the column.

Comparative Example 2

An aqueous acrylic acid solution was subjected to an operation of azeotropic distillation by following the procedure of Example 1 while changing the amount of 4-hydroxy-2,2,6,6-tetramethylpiperidinooxyl to 120 ppm and omitting the use of 4-dihydroxy-2,2,6,6-tetramethylpiperidine.

When the azeotropic separating column 40 was continuously operated under the conditions, the same state of separation as formed in Example 1 was obtained. On the 20th day of starting the operation, the pressure drop of the column in side was recognized. On the 24th day of the operation, the operation could be continued only with difficulty. When the operation was stopped and the distilling column was disassembled and inspected, the occurrence of a large amount of a polymer was recognized in the stripping section of the interior of the column.

Comparative Example 3

An aqueous acrylic acid solution was subjected to an operation of azeotropic distillation by following the procedure of Example 1 while changing the amount of 4-hydroxy-2,2,6,6-tetramethylpiperidinooxyl to 120 ppm and omitting the use of ammonium salt of N-nitrosophenylhydroxylamine.

When the azeotropic separating column 40 was continuously operated under the conditions, the same state of separation as formed in Example 1 was obtained. On the 10th day of starting the operation, the pressure drop of the column inside was recognized. On the 12th day of the operation, the operation could be continued only with difficulty. When the operation was stopped and the distilling column was disassembled and inspected, the occurrence of a large amount of a polymer was recognized in the stripping section of the interior of the column.

Comparative Example 4

An aqueous acrylic acid solution was subjected to an operation of azeotropic distillation by following the procedure of Example 1 while changing the amount of 1,4-dihydroxy-2,2,6,6-tetramethylpiperidine to be used to 60 ppm, that of 4-hydroxy-2,2,6,6-tetramethylpiperidine to 50 ppm, and that of the ammonium salt of N-nitrosophenylhydroxylamine to 50 ppm and omitting the use of 4-hydroxy-2,2,6,6-tetramethylpiperidinooxyl.

When the azeotropic separating column 40 was continuously operated under the conditions, the same state of separation as formed in Example 1 was obtained during the first stage of operation. On the 8th day of starting the operation, the pressure drop of the column inside was recognized. On the 10th day of the operation, the operation could be continued only with difficulty. When the operation was stopped and the distilling column was disassembled and inspected, the occurrence of a large amount of a polymer was recognized in the stripping section of the interior of the column.

Comparative Example 5

An aqueous acrylic acid solution was subjected to an operation of azeotropic distillation by following the procedure of Example 1 while changing the amount of 4-hydroxy-2,2,6,6-tetramethylpiperidiooxyl to be used to 140 ppm and omitting the use of 1,4-dihydroxy-2,2,6,6-tetramethylpiperidine and 4-hydroxy-2,2,6,6-tetramethylpiperidine. When the azeotropic separating column 40 was continuously operated under the conditions, the same state of separation as formed in Example 1 was obtained during the initial stage of operation. On the 15th day of starting the operation, the pressure drop of the column inside was recognized. On the 18th day of the operation, the operation could be continued only with difficulty. When the operation was stopped and the distilling column was disassembled and inspected, the occurrence of a large amount of a polymer was recognized in the stripping section of the interior of the column.

What is claimed is:

1. A method for preventing the polymerization of (meth) acrylic acid and esters thereof, comprising the step of using (i) an N-nitrosophenylhydroxylamine or a salt thereof, (ii) an N-oxyl compound, (iii) an N-hydroxy-2,2,6,6-tetramethylpiperidine compound, and (iv) a 2,2,6,6-tetramethylpiperidine compound in combination in a purifying column.

2. A method according to claim 1, wherein the salt of N-nitrosophenylhydroxylamine is the ammonium salt of an N-nitrosophenylhydroxylamine.

3. A method according to claim 1, wherein said N-nitrosophenylhydroxylamine or a salt thereof is supplied to a purifying column from a level not higher than the position of 70% of the total number of theoretical plates, with the bottom side of the column as the base point.

4. A method for the production of (meth)acrylic acid or an ester thereof, characterized by incorporating in the process of production the method for the prevention of the polymerization of (meth)acrylic acid and esters thereof as set forth in claim 1.

* * * * *